US00RE38659E

(19) United States
(12) Reissued Patent
Williams

(10) Patent Number: US RE38,659 E
(45) Date of Reissued Patent: Nov. 23, 2004

(54) ESTERS WITH MUSKY ODOR AND THEIR USE IN PERFUMERY

(75) Inventor: Alvin S. Williams, Nyon (CH)

(73) Assignee: Firmenich SA, Geneva (CH)

(21) Appl. No.: 10/326,341

(22) Filed: Dec. 23, 2002

Related U.S. Patent Documents

Reissue of:
(64) Patent No.: 6,384,269
Issued: May 7, 2002
Appl. No.: 09/553,376
Filed: Apr. 20, 2000

U.S. Applications:
(63) Continuation of application No. PCT/IB99/01469, filed on Aug. 25, 1999.

(30) Foreign Application Priority Data

Sep. 9, 1998 (CH) ..... 1841/98

(51) Int. Cl.[7] ..... C07C 67/02; C07C 69/02
(52) U.S. Cl. ..... 560/249; 514/506; 560/231; 560/126; 560/198
(58) Field of Search ..... 514/506; 560/198, 560/126, 231, 249

(56) References Cited

U.S. PATENT DOCUMENTS 5,166,412 A * 11/1992 Giersch et al. ..... 560/231

FOREIGN PATENT DOCUMENTS

DE 1923223 * 11/1969
EP 0472966 * 3/1992

OTHER PUBLICATIONS

Kawai, Y. et al. Bioorganic Chemistry 27, (1999), pp. 3–19.*
Givaudan et al. (DN 72:54884, CAPLUS, abstract of DE 1,923,223).*
H.R. Ansari, Tetrahederon, vol. 29, pp. 1559–1564 (1973).*
G. Lhommet et al., Synthetic Communications, vol. 26, No. 21, pp. 3897–3901 (1996).*
Givaudan et al. (DN 72:54884 CAPLUS, abstract of DE 1923223), 1969.*
H.R. Ansari, "Cyclisation of Optically Active Dihydromyrcenes (2,6–Dimethyl–2, 7–Octadiene)", *Tetrahedron*, vol. 29, pp. 1559–1564 (1973).*
G. Lhommet et al., "A General and Versatile Synthesis of 4– and 5–Oxoacids", *Synthetic Communications*, vol. 26, No. 21, pp. 3897–3901 (1996).*

* cited by examiner

*Primary Examiner*—Sabiha Qazi
(74) *Attorney, Agent, or Firm*—Winston & Strawn LLP

(57) ABSTRACT

The compounds of formula (I)

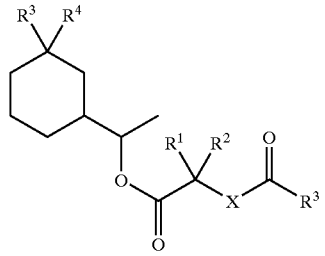

in which the symbols $R^1$, $R^2$, $R^3$ and $R^4$ represent independently from each other a hydrogen atom or a methyl or ethyl group, the symbol X represents an oxygen atom or an alkylene group of formula

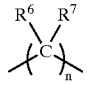

in which n is an integer from 1 to 3, the symbols $R^6$ and $R^7$ represent each a hydrogen atom or a methyl or ethyl group, and $R^5$ represents an alkyl or alkoxy group from $C_1$ to $C_4$, linear or branched, an alkenyl group from $C_2$ to $C_4$, linear or branched, or a group of formula

—(O)C—Y—$R^8$ in which Y has the same meaning as X and $R^8$ is a linear or branched alkyl group from $C_1$ to $C_4$ or a linear or branched alkenyl group from $C_2$ to $C_4$, are novel compounds showing musky odors and which confer musky-velvety, voluminous and very tenacious notes to the products to which they are added.

10 Claims, No Drawings

ESTERS WITH MUSKY ODOR AND THEIR USE IN PERFUMERY

Matter enclosed in heavy brackets [ ] appears in the original patent but forms no part of this reissue specification; matter printed in italics indicates the additions made by reissue.

CROSS REFERENCE TO RELATED APPLICATION

This application is a continuation of international application no. PCT/IB99/01469 filed on Aug. 25, 1999.

TECHNICAL FIELD AND PRIOR ART

The present invention relates to the field of perfumery. It relates, more particularly, to esters derived from 1-(3,3-dimethyl-1-cyclohexyl)-1-ethanol which have remarkable odor properties.

We have found that the esters according to the present invention and as defined in the formula (I) below, show useful and prized odor properties and that, as a result, they can be used for the preparation of perfumes, perfuming compositions and perfumed articles. They are employed in order to confer musky type odor effects.

In the field of the synthesis of compounds having musky odors, there has been great activity for the last ten years, resulting from the need to find novel musky odor compounds which can replace certain compounds of widespread use in perfumery and which use is becoming more and more restricted due to toxicological and ecological reasons. The esters according to the present invention are products which fulfil the requirements for perfuming compounds, and they are capable of replacing the above-mentioned known compounds.

The prior art, in particular the application DE-OS 1 923 223, discloses certain esters derived from 1-(3,3-dimethyl-1-cyclohexyl)-ethanol. However, there is no mention of a musky odor from any of the compounds disclosed. The olfactive character of the known compounds is generally described as being of the floral-woody type.

On the other hand, U.S. Pat. No. 5,166,412 discloses compounds of the type (II)

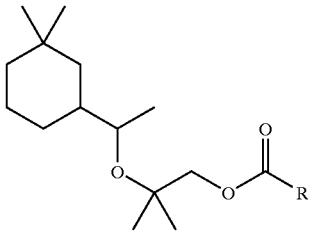

wherein R is an alkyl group from $C_1$ to $C_3$, and which show an odor of the musky type characterized by an intense note of the type ambrette seeds, fruity-pear, reminiscent of the odor of Williams pears.

We have now surprisingly found that the compounds described by formula (I) defined below have musky odors which are quite distinct from those of the compounds of the above formula (II), and which are very much appreciated in perfumery.

DESCRIPTION OF THE INVENTION

The object of the present invention is therefore to provide new compounds which are useful as perfume ingredients, to impart odors of the musky type.

This object is attained by the compounds of formula (I)

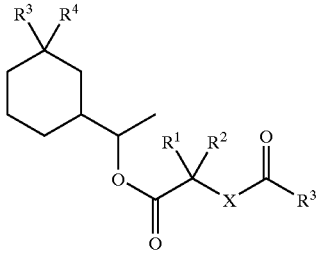

in which the symbols $R^1$, $R^2$, $R^3$ and $R^4$ represent independently from each other a hydrogen atom or a methyl or ethyl group, the symbol X represents an oxygen atom or an alkylene group of formula

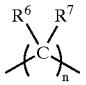

in which n is an integer from 1 to 3, the symbols $R^6$ and $R^7$ represent each a hydrogen atom or a methyl or ethyl group, and $R^5$ represents an alkyl or alkoxy group from $C_1$ to $C_4$, linear or branched, an alkenyl group from $C_2$ to $C_4$, linear or branched, or a group of formula $$—(O)C—Y—R^8$$

in which Y has the same meaning as X and $R^8$ is a linear or branched alkyl group from $C_1$ to $C_4$ or a linear or branched alkenyl group from $C_2$ to $C_4$.

According to a preferred embodiment of the invention, there will be used compounds of the general formula (III)

(III)

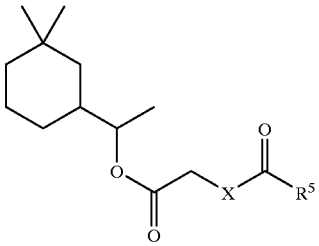

in which X is an oxygen atom or an unsubstituted methylene or ethylene group and $R_5$ is a group as defined in formula (I) and having 1 to 3 carbon atoms.

The esters of the above formulae (I) and (III) are novel compounds.

Another object of the invention is the use of the compounds of the above formulae in perfumery, as well as the perfumes perfuming compositions and perfumed articles containing these compounds.

The compounds of the invention show musky odor notes in which a slight fruity-ambrette connotation is found, which however is clearly less pronounced than in the compounds of the prior art, namely those according to formula (II). The global olfactive impression of the compounds of the present invention is generally that of musky odor compounds having a sweet and heavy connotation, close to that of the so-called polycyclic musks, quite unlike that of the compounds of formula (II) which show lighter and less tenacious olfactive notes.

The compounds of the invention can be present in the form of 4 stereoisomers in the pure state or as a mixture of the stereoisomers. The invention thus includes all these possible mixtures and all the possible individual isomers. As the olfactive note of each of these isomers can of course be different from that of the others, the odor of every possible isomer mixture can also change as a function of the content of any given diastereomer or enantiomer.

We have moreover been able to establish that within the above-identified preferred compounds of the invention according to formula (III), the best olfactive characteristics were represented in the isomers of the esters of the present invention derived from the alcohol (+)-(1S, 1'R)-1-(3',3'-dimethyl-1'-cyclohexyl)-1-ethanol, which is used as a starting product for the synthesis of some of the compounds of the invention.

As the most preferred compound of the invention, there is cited in particular 1-[(3,3-dimethyl-1-cyclohexyl) ethoxycarbonyl]methyl propanoate. This compound possesses a classical musky type odor, reminiscent of that of Galaxolide® (7,8-dihydro-4,6,6,7,8,8-hexamethyl-6H-cyclopenta[9]-2-benzopyrane; trademark of International Flavors and Fragrances, USA), and confers an olfactive impression which is that of a sweet and natural musky odor, with a velvety connotation, and which provides much volume. There is also found a light ambrette nuance which is accompanied by an undernote reminiscent of the odor of green fruits. When compared to the odor of the compounds according to the prior art, this compound of the invention develops a musky odor which is distinctly more tenacious and heavier than those of known compounds, which makes it particularly useful for the creation of base notes in perfumes and perfuming compositions of musky odor.

The above-described odor properties are best represented in the isomer of the configuration (1S, 1'R), namely (1S, 1'R)-1-[(3',3'-dimethyl-1'-cyclohexyl) ethoxycarbonyl] methyl propanoate, which renders this compound a choice ingredient of the invention.

Moreover, the mixtures containing a preponderant amount of this isomer together with its enantiomer or with its other stereoisomers give appreciated odor effects. Accordingly, mixtures containing a preponderant amount of this most preferred isomer of the invention are also a preferred embodiment of the invention.

The compounds of the invention can be used in practically all fields of modern perfumery. There can be cited here applications in fine perfumery, namely for the preparation of perfumes and colognes in which original olfactive effects can be obtained.

The compounds can also be used in functional perfumery. Non-limiting examples for this type application include soaps, bath and shower gels, shampoos and other hair care products, deodorants and an antiperspirants, air fresheners, liquid and solid detergents for the treatment of textiles, fabric softeners, or all purpose cleaners.

In these applications, the compounds (I) and (III) can be used alone or in admixture with other perfuming ingredients, solvents or adjuvants of current use in perfumery. The nature and the variety of these coingredients do not require a more detailed description here, which, moreover, would not be exhaustive, and the person skilled in the art will be able to choose the latter through its general knowledge and as a function of the nature of the product to be perfumed and of the desired olfactive effect. These perfuming ingredients belong to chemical classes as varied as alcohols, aldehydes, ketones, esters, ethers, acetates, nitrites, terpene hydrocarbons, sulfur- and nitrogen-containing heterocyclic compounds, as well as essential oils of natural or synthetic origin. A large number of these ingredients is moreover listed in reference textbooks such as the book of S. Arctander, Perfume and Flavor Chemicals, 1969, Montclair, N.J., USA, or its more recent versions, or in other works of similar nature.

The proportions in which the compounds according to the invention can be incorporated in the various products mentioned beforehand vary within a large range of values. These values depend on the nature of the article or product that one desires to perfume and the olfactive effect searched for, as well as on the nature of the coingredients in a given composition when the compounds of the invention are used in admixture with perfuming coingredients, solvents or adjuvants of current use in the art.

As an example, there can be cited typical concentrations of the order of 5 to 10%, or even 20%, by weight of these compounds relative to the weight of the perfuming composition in which it is incorporated. Far lower concentrations than those mentioned can be used when the compound (I) or (III) is directly applied for the perfuming of the various consumer products cited beforehand.

The compounds of the invention are generally prepared by esterification of an alcohol of formula (IV) below with the respective acid of formula (V), or an appropriate derivative of it. The reaction is illustrated in the following scheme I, in which the symbols $R^1$ to $R^5$ and X have the meaning indicated in formula (I).

Scheme I

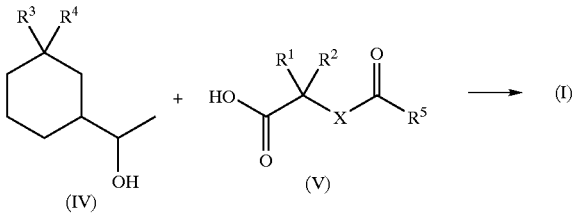

As an appropriate derivative of the acid (V), there can, for example, be cited the acid halides, like the chloride. Other appropriate derivatives are known to a person skilled in the art. In case one wants to synthesize an optically active compound of formula (I), there will be used the corresponding optically active alcohol of formula (IV) in the esterification reaction. According to a preferred embodiment of the invention, there will be used 1-(3,3-dimethyl-1-cyclohexyl)-1-ethanol or one of its enantiomers as starting alcohol for the preparation of the preferred compounds of the invention.

Where the acids of formula (V), respectively an appropriate derivative thereof, are not available or do not react as wanted, there can be used an alcohol of formula (VI) below in which X is an oxygen atom and the symbols $R_1$ to $R^4$ have the meaning indicated in formula (I), in an esterification reaction with an acid of formula (VII) in which $R^5$ has the meaning given in formula (I), or, respectively, with an appropriate derivative of this acid, such as, for example, a halide.

Scheme II

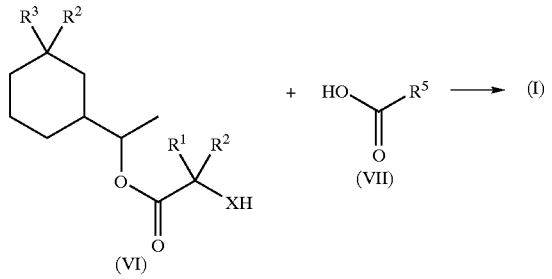

X = O

The alcohols of formula (VI) can be obtained by saponification of certain compounds of the invention of formula (I) in which X is an oxygen atom.

In the methods described above for the preparation of the compounds of the invention, the stereochemistry of the alcohols (IV) and (VI) is retained. The stereochemistry of the compounds of the invention is thus that of the alcohols used as starting products.

The specific reaction conditions will now be described in the following examples in which the abbreviations have the usual meaning in the art and the temperatures are given in degrees Celsius (°C); the NMR spectral data (chemical shift δ) are given in ppm relative to TMS as an internal standard. The invention will also be illustrated by examples describing the use of the compounds of the invention in perfumery.

EMBODIMENTS OF THE INVENTION

EXAMPLE 1

Preparation of the Compounds of Formula (I)

a) (1S,1'R)-1-[(3',3'-Dimethyl-1'-cyclohexyl) ethoxycarbonyl]methyl Propanoate 3 g of (1S,1'R)-1-(3',3'-dimethyl-1'-cyclohexyl)-1-ethanol (prepared from (+)-β-citronellene (Fluka) according to the process described by H. R. Ansari, Tetrahedron 29, 1559 (1973), $[\alpha]^{20}_{D}$=+11.6°, containing about 17% of other stereoisomers, or bought from DRT, France) and 1.52 g of pyridine were dissolved in 50 ml of diethyl ether. There were then added 2.9 g of 2-chloro-2-oxoethyl propanoate (prepared according to F. K. Thayer, Organic Synthesis Col. Vol. 1 (1932), p. 12), dissolved in 20 ml of diethyl ether over 10 minutes. The reaction mixture was then stirred for 30 minutes, after which another portion of 2-chloro-2-oxoethyl propanoate was added. After 1 h reaction time, the reaction was quenched by adding 5 ml of aqueous HCl (1 M), and the mixture was extracted with ether. After flash column chromatography of the extract and concentration of the solution, the thus-obtained crude product was distilled at 120°/9×$10^2$ Pa to obtain (1S,1'R)-1-[(3',3'-dimethyl-1'-cyclohexyl) ethoxy-carbonyl]methyl propanoate. The yield was 4.12 g (79.5%)

NMR($^1$H): 4.78(1 H, quintet, J=6.3 Hz); 4.58(2H, s); 2.45(2H, q, J=7.5Hz); 1.7–0.7(9H, m); 1.18(3H, t, J=7.5 Hz); 1.16(3H, d, J=6.3 Hz); 0.89(3H, s) 0.85(3H, s). NMR ($^{13}$C): 173.7(s); 167.6(s); 76.3(d); 60.8(t); 41.1(t); 39.1(t); 38.3(d); 33.5(q); 30.5(s); 28.3(t); 27.2(t); 24.6(q); 21.9(t); 17.0(q); 9.0(q). MS: 57(100), 123(77), 69(69), 115(68), 83(57), 138(44), 95(42), 109(40).

When there was used, in the preparation mode described under a), (1R,1'S)-1-(3',3'-dimethyl-1-cyclohexyl)-1-ethanol [<<(−)-cyclademol>>; origin DRT, France; $[\alpha]^{D}_{20}$=−10.4°, containing about 18% of other stereoisomers], there was obtained (1R,1'S)-1-[(3',3'-dimethyl-1-cyclohexyl)ethoxycarbonyl]methyl propanoate, the analytical data of which (NMR, MS) were identical to those given under a).

b) (1S,1'R)-1-[(3',3'-Dimethyl-1'-cyclohexyl) ethoxycarbonyl]methyl Butanoate

The reaction was carried out as described above under a), using 4.78 g of 2-chloro-2-oxoethyl butanoate (prepared according to the above-cited literature). The yield was 5.22 g (95.8%) of a product having a boiling point of 120°/6×$10^2$ Pa.

NMR($^1$H): 4.78(1H, quintet, J=6.3 Hz); 4.60(2H, s); 2.40(2H, t, J=7.5 Hz); 1.70(2H, m, J=7.5 Hz); 1.75–0.75(9H, m); 1.18(3H, d, J=6.3 Hz); 0.99(3H, t, J=7.5 Hz); 0.91(3H, s); 0.87(3H, s). NMR($^{13}$C): 173.0(s); 167.7(s); 76.3(d); 60.7(t); 41.1(t); 39.1(t); 38.4(d); 35.7(t); 33.5(q); 30.5(s); 28.3(t); 24.7(q); 21.9(t); 18.4(t); 17.0(q); 13.6(q). MS: 71(100), 123(81), 69(79), 83(68), 43(58), 109(54), 129(52), 95(49).

c) (1S,1'R)-1-(3',3'-Dimethyl-1'-cyclohexyl)ethyl 4-oxohexanoate 1.09 g (8.4 mmole) of 4-oxo-hexanoic acid (prepared according to G. L. Hommet et al., Synth. Commun., 26, 3897 (1996)) were mixed with 1.25 g (8 mmole) of (1S, 1'R)-1-(3',3'-dimethyl-1-cyclohexyl)-1-ethanol, and p-toluenesulfonic acid (0.012 g) in 70 ml of toluene. The reaction mixture was heated under reflux over 15 h in a Dean-Stark type separator. The thus-obtained solution was washed with water, saturated $NaHCO_3$ solution and again with water, before the solvent was removed under reduced pressure. After distillation in a bulb-to-bulb apparatus at 140°/5×$10^2$ Pa, there were obtained 0.84 g (39%) of the product.

NMR($^1$H): 4.68(1H, quintet, J=6.3 Hz); 2.71(2H, m); 2.58(2H, m); 2.48(2H, q, J=7.5 Hz); 1.7–0.7(9H, m); 1.14 (3H, d, J=6.3 Hz); 1.03(3H, t, J=7.5 Hz); 0.91(3H, s); 0.88(3H, s). NMR($^{13}$C): 209.4; 172.5; 75.1; 41.3; 39.1; 38.3; 36.7; 35.9; 33.5; 30.5; 28.4; 28.3; 24.6; 22.0; 17.1; 7.8. MS: 113(100), 138(31), 123(28), 83(23), 139(22), 69(19), 95(19), 57(17).

d) (1S,1'R)-1-(3',3'-Dimethyl-1-cyclohexyl)ethyl 5-oxohexanoate

To a solution of 2.00 g (12.8 mmole) of (1S,1'R)-1-(3',3'-dimethyl-1-cyclohexyl)-1-ethanol, 1.66 g (12.8 mmole) of 5-oxo-hexanoic acid and 0.26 g of 4-dimethylaminopyridine in 20 ml of dichloromethane, there were added 2.06 g (14.1 mmole) of dicyclohexylcarbodiimide. The solution was stirred over 90 min, filtered over Celite®, dried over $MgSO_4$ and filtered. After evaporation of the solvent, there was obtained a yellow oil (3.0 g) which was distilled in a bulb-to-bulb apparatus at 160°/1×$10^3$ Pa, to obtain 2.12 g (62%) of the desired product.

NMR($^1$H): 4.69(1 H, quintet, J=6.3 Hz); 2.51(2H, t, J=7.1 Hz); 2.32(2H, t, J=7.1 Hz); 2.14(3H, s); 1.89(2H, quintet, J=7.1 Hz); 1.7–1.0(9H, m); 1.15(3H, d, 6.3 Hz); 0.90(3H, s); 0.87(3H, s). NMR($^{13}$C): 208.0; 172.8; 74.8; 42.6; 41.4; 39.1; 38.3; 33.6; 33.5; 30.5; 29.9 28.4; 24.6; 22.0; 19.1; 17.2. MS: 113(100), 123(31), 85(30), 138(29), 43(22), 69(22), 130 (20), 55 (19).

e) (1S,1'R)-[1-(3',3'-Dimethyl-1'-cyclohexyl) ethoxycarbonyl]methyl Methyl Oxalate i) (1S,1'R)-1-(3',3'-Dimethyl-1'-cyclohexyl)ethyl Hydroxyacetate This alcohol was prepared by saponification of (1S,1'R)-1-[3',3'-dimethyl-1'-cyclohexyl)ethoxycarbonyl]methyl propanoate. To this end, 50.0 g (185 mmol) of this compound were dissolved in 250 ml of methanol in a 500 ml flask. After cooling of the mixture to −780°, a solution containing about 5.4 M of sodium methoxide in methanol (34.3 ml, 185 mmol) was added over 30 min, stirring was then continued over 90 min at −50° and the reaction mixture was then neutralized with 100 ml of aqueous HCl (2 M) at this temperature. The mixture was extracted with diethyl ether and washed to neutrality with a saturated $NaHCO_3$ solution and then water. After drying and concentration of the organic phase, the crude product was distilled on a Vigreux type column at 62°/5×$10^2$ Pa to obtain 23.65 g (60%) of the desired product.

NMR($^1$H): 4.81(1H, quintet, J=6.3 Hz); 4.11(2H, m); 2.70(1H, large s); 1.7–0.7(9H, m); 1.20(3H, d, J=6.3 Hz); 0.91(3H, s); 0.88(3H, s). NMR($^{13}$C): 173.1(s); 76.2(d); 60.7(t); 41.3(t); 39.0(t); 38.3(d); 33.5(q); 30.5(s); 28.1(t); 24.6(q); 21.9(t); 17.1(q). MS: 69(100), 123(71), 83(68), 55(67), 41(63), 31(51), 95(49), 45(46).

The compound was then esterified as described below, under ii).

ii) 2 g of the product obtained under i) (9.4 mmol) and mixed with 1.1 g (14 mmol) of pyridine in 25 ml of diethyl ether were esterified by the dropwise addition of 1.7 g (14 mmol) of methyl chlorooxalate over 10 min. The temperature was maintained at 30° with an ice bath, and the mixture was stirred over 30 min, then hydrolyzed with 3 ml of aqueous HCl (2 M). The ether phase was washed with a saturated $NaHCO_3$ solution, then with water. After drying and filtration, the solution was concentrated and distilled in a bulb-to-bulb apparatus at 140°/3×$10^2$ Pa, to obtain 2.59 g (92%) of the product.

NMR($^1$H): 4.80(1H, m); 4.78(2H, s); 3.94(3H, s); 1.7–0.7 (9H, m); 1.18(3H, d, J=6.3Hz); 0.91(3H, s); 0.87(3H, s). NMR($^{13}$C): 165.8(s); 157.4(s); 156.8(s); 77.2(d); 62.5(t); 53.8(q); 41.0(t); 39.0(t); 38.3(d); 33.5(q); 30.5(s); 28.3(t); 24.5(q); 21.9(t); 17.0(q). MS: 123(100), 69(49), 138(44), 95(34), 109(33), 139(30), 83(27), 111(27).

f) (1S,1'R)-1-[(3',3'-Dimethyl-1-cyclohexyl) ethoxycarbonyl]methyl 2-propenoate

This compound was prepared from the alcohol (1S,1'R)-1-(3',3'-dimethyl-1-cyclohexyl)ethyl hydroxyacetate, obtained as described under 1)e)i). 1 g (4.67 ml) of this alcohol were added at 0° and over a period of 10 min to a suspension prepared from 0.21 g (5.14 mmol) of a 60% suspension of NaH in mineral oil and 20 ml of THF. The suspension was stirred at room temperature over 30 min, then 0.47 g (5.14 mmole) of acryloyl chloride were added after the mixture had been cooled to −20°. The mixture was warmed to room temperature and stirred for 5 h at that temperature, before another 0.47 g (5.14 mmol) of acryloyl chloride and 0.21 g of a 60% suspension of NaH in mineral oil were added. Stirring was continued for 2 h, then the reaction was quenched with water and the solution extracted with ether. The organic extract was washed with aqueous HCl (1 M), a saturated $NaHCO_3$ solution and water and dried over $MgSO_4$. After evaporation of the solvent, the crude product was distilled in a bulb-to-bulb apparatus at 120°/4×$10^2$ Pa, to obtain 1.13 g (90%) of the desired product. NMR($^1$H): 6.52(1H, d, J=17.4 Hz); 6.21(1H, dd, J=10.7, 17.4 Hz); 5.93(1H, 10.3Hz); 4.79(1H, m); 4.68(2H, s); 1.8–0.8(9H, m); 1.20(3H, d, 6.4 Hz); 0.90(3H, s); 0.87 (3H, s). NMR($^{13}$C): 167.4(s); 165.4(s); 132.0(t); 127.5(d); 76.4(d); 61.0(t); 41.0(t); 39.0(t); 38.3(d); 33.5(q); 30.5(s); 28.3(t); 24.6(q); 21.9(t); 17.0(q). MS: 123(100), 55(76), 138(68), 113(64), 109(63), 69(59), 95(50), 83(46).

g) (1S, 1'R)-1-[(3',3'-Dimethyl-1-cyclohexyl) ethoxycarbonyl]methyl 2-butenoate

This compound was prepared as described above, under f), replacing acryloyl chloride by crotonoyl chloride (0.49 g, 4.67 mmol) which was added at room temperature. After drying and evaporation of the solvent, there were obtained 1.43 g of an oil which was chromatographed over silica, followed by a distillation in a bulb-to-bulb apparatus at 120°/4×$10^2$ Pa, to provide 0.83 g (71%) of the desired product.

NMR($^1$H): 7.06(1H, m), 5.94(1H, d, J=15.9 Hz); 4.78(1H, quintet, J=6.0 Hz); 4.65(2H, d); 1.91(3H, d, J=6.7 Hz); 1.7–1.0(9H, m); 1.19(3H, d, J=6.3 Hz); 0.90(3H, s); 0.87 (3H, s). NMR($^{13}$C): 167.7; 165.6; 146.3; 121.7; 76.3; 60.8; 41.0; 39.1; 38.3; 33.5 30.5; 28.3; 24.6; 21.9; 18.1; 17.0. MS: 69(100), 123(67), 138(56), 127(49), 109(45), 83(42), 95(33), 139 (25).

EXAMPLE 2

Preparation of a Perfuming Composition

A base perfuming composition was prepared from the following ingredients:

| Ingredients | Parts by weight |
|---|---|
| Amyl acetate | 50 |
| (E)-3-Hexenyl acetate | 10 |
| γ-Undecalactone | 300 |
| Ethyl butyrate | 50 |
| Allyl cyclohexylpropanoate | 50 |
| 10% *α-Damascone | 150 |
| Allyl heptanoate | 300 |
| Phenoxyethyl Isobutyrate | 1500 |
| 4-tert-Butyl-cyclohexyl acetate[1)] | 500 |
| Hedione ®[2)] | 300 |
| Jasmolactone[3)] | 40 |
| Hexyl salicylate | 1000 |
| Veloutone[4)] | 50 |
| 2-tert-Butyl-1-cyclohexyl acetate | 2500 |
| α-Ionone | 150 |
| 2,4-Dimethyl-3-cyclohexene-1-carbaldehyde[5)] | 150 |
| Total | 7000 |

*in dipropylene glycol
[1)]origin: Firmenich SA. Geneva, Switzerland
[2)]methyl dihydrojasmonate: origin: Firmenich SA Geneva, Switzerland
[3)](E)-8-decen-5-olide; origin: Firmenich SA. Geneva, Switzerland
[4)]2,5,5-trimethyl-5-pentyl-1-cyclopentanone; origin: Firmenich SA. Geneva, Switzerland
[5)]origin: Firmenich SA. Geneva, Switzerland To this base composition of the apple type, there were added 2000 parts by weight of 1-[(3,3-dimethyl-1-cyclohexyl)ethoxycarbonyl]methyl propanoate. There was thus obtained a novel composition in which the fruity aspect was clearly stronger with respect to the base composition. Furthermore, the composition containing the compound of the invention possessed an appreciated and very natural velvety-musky connotation, the compound having also imparted far more volume to the odor of the base composition. The perfumers found furthermore that the diffusion of the composition had become superb, both as regards its top note and its heart note, and in particular as regards the bottom note, thanks to the tenaciousness and the heavy character of this musky compound.

The above-described odor effect was particularly pronounced and rich when the isomer of the configuration (1S,1'R) was used.

When the compound of the invention was replaced by (1S,1'R)-2-[1-(3',3'-dimethyl-1'-cyclohexyl)ethoxy]-2-methylpropyl propanoate (described in application EP 472 966), there was observed a different effect, the resulting composition being less heavy and velvety, thus underlining less the fruity-apple aspect and showing a diffusion of the bottom note which was less pronounced and voluminous. In a general way, this known composition was lighter, less tenacious and less musky-heavy than the composition containing the compound of the invention.

EXAMPLE 3

Preparation of a Perfuming Composition

A base perfuming compositions was prepared from the following ingredients:

| Ingredients | Parts by weight |
|---|---|
| Hexyl acetate | 50 |
| Tetramethylnonyl acetate[1)] | 1500 |
| TCD acetate[2)] | 1500 |
| Methyl cinnamate | 250 |
| 10% *γ-Decalactone | 200 |
| γ-Dodecalactone | 50 |
| 50% *β-Damascone | 250 |
| Isopentyrate[3)] | 100 |
| Myroxyde ®[4)] | 100 |
| Veloutone[5)] | 700 |
| 10% *Bourgeonal ®[6)] | 300 |
| 10% *Lilial ®[7)] | 2700 |
| 1% *n-Octanal | 100 |
| Mayol ®[8)] | 200 |
| Total | 8000 |

*in dipropylene glycol (DIPG)
[1)]origin: Firmenich SA. Geneva, Switzerland
[2)]tricyclo(5,2,1,0[2,6])dec-4-yl)methyl acetate; origin: Firmenich SA. Geneva, Switzerland
[3)]1,3-dimethyl-3-butenyl isobutyrate origin: Firmenich SA. Geneva, Switzerland
[4)]isomer mixture of ocimene epoxide; origin: Firmenich SA. Geneva, Switzerland
[5)]see Example 2
[6)]3-(4-tert-butyl-1-phenyl)propanol; origin: Quest International
[7)]3-(4-tert-butyl-1-phenyl)-2-methylpropanol; origin: Givaudan-Roure SA, Vernier, Switzerland
[8)]1-hydroxymethyl-4-isopropyl cyclohexane; origin: Firmenich SA. Geneva, Switzerland When there were added to this base composition with a fruity, pear type odor 2000 parts by weight of 1-[(3,3-dimethyl-1-cyclohexyl)ethoxycarbonyl]methylpropanoate, there was obtained a novel composition, the odor of which was considerably modified with respect to the note of the base composition. The modification was mainly apparent in the fruity-pear connotations, which had aquired a rich and full character and a pronounced and elegant volume, recalling the odor of a ripe pear. This voluminous impression persisted during the slow evaporation of the composition over time, thus prolongating the fruity and elegant tonality of the composition. This fragrance effect was particularly marked and rich when the isomer of (1S,1'R)-configuration was added to the base composition.

EXAMPLE 4

Preparation of a Perfuming Composition for a Powder Detergent

A base perfuming composition for a powder detergent was prepared by mixing the following ingredients:

| Ingredients | Parts by weight |
|---|---|
| Citronellyl acetate | 200 |
| Amylcinnamic aldehyde | 1000 |
| Hexylcinnamic aldehyde | 2000 |
| 10% *Ambrox ® DL[1)] | 100 |
| Isononyl acetate | 200 |
| Verdyl acetate | 400 |
| Verdyl propionate | 500 |
| 10% *Intreleven aldehyde[2)] | 100 |
| 10% *Aldehyde 13—13[3)] | 200 |
| Coumarin | 100 |
| Lilial ®[4)] | 1000 |
| 4-tert-Butyl-cyclohexyl acetate[5)] | 1300 |
| Fleuramone ®[6)] | 200 |
| 3-Methyl-5-phenyl-1-pentanol[7)] | 500 |
| Hexyl salicylate | 700 |
| Tetrahydromuguol[8)] | 400 |
| 10% *α-Damascone | 250 |
| Polywood ®[9)] | 150 |
| Iralia ®[10)] total | 300 |
| Vertofix coeur[11)] | 400 |
| Total | 10000 |

*in DIPG
[1)]racemic tetramethyl perhydronaphthofurane; origin: Firmenich SA. Geneva, Switzerland
[2)]isomer mixture of undecenal; origin: International Flavors & Fragrances, USA
[3)]tridecanal and 11-methyldodecanal; origin: Firmenich SA. Geneva, Switzerland
[4)]see Example 3
[5)]see Example 2
[6)]2-heptyl-1-cylopentanone; origin: International Flavors & Fragrances, USA
[7)]origin: Firmenich SA. Geneva, Switzerland
[8)]isomeric mixture; origin: International Flavor & Fragrances, USA
[9)]perhydro-5,5,8a-trimethyl-3-naphthyle acetate; origin: Firmenich SA. Geneva, Switzerland
[10)]mixture of iso-methyl ionones; origin: Firmenich SA. Geneva, Switzerland
[11)]origin: International Flavors & Fragrances, USA When there were added to this base perfuming composition intended for a powder detergent 1000 parts by weight of 1-[(3,3-dimethyl-1-cyclohexyl)ethoxycarbonyl]methyl propanoate, there was obtained a novel composition, the olfactive note of which had aquired a very remarkable volume and tenaciousness. The typical odor impression conferred by the aldehydes in the base composition was well sustained by the musky-heavy note of the compound of the invention. The perfumers also found that the diffusion of the composition had become stronger, putting an accent on the fruity and rose tonality of the composition.

The above-described fragrance effects are perceptible both from the novel composition and on linen washed with a powder detergent perfumed with that said composition. The musky aspect of the odoriferous note of the composition according to the invention, which could also be smelled on the thus-treated linen, was similar to the notes typically conferred by polycyclic musky odor compounds of the indane type, i.e. a bewitching, warm, powdery, slightly animal and velvety connotation. The best olfactive effect was obtained with the preferred compound of the invention, namely the (1S,1'R)-isomer of the above-identified compound. The musky effect observed by our perfumers was olfactively closest to that typically conferred by Galaxolide®, under similar application conditions.

What is claimed is:

1. A compound of formula (I)

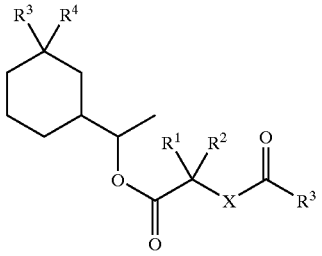

in which the symbols $R^1$, $R^2$, $R^3$ and $R^4$ represent independently from each other a hydrogen atom or a methyl or ethyl group, the symbol X represents an oxygen atom or an alkylene group of formula

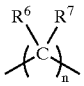

in which n is an integer from 1 to 3, the symbols $R^6$ and $R^7$ represent each a hydrogen atom or a methyl or ethyl group, and $R^5$ represents an alkyl or alkoxy group from $C_1$ to $C_4$, linear or branched, an alkenyl group from $C_2$ to $C_4$, linear or branched, or a group of formula $$—(O)C—Y—R^8$$

in which Y has the same meaning as X and $R^8$ is a linear or branched alkyl group from $C_1$ to $C_4$ or a linear or branched alkenyl group from $C_2$ to $C_4$.

2. A compound according to claim 1, of formula (III)

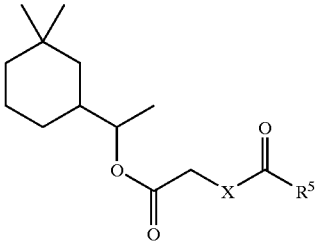

wherein X is an oxygen atom or an unsubstituted methylene or ethylene group and $R^5$ is a group as defined in claim 1 and having from 1 to 3 carbon atoms.

3. A compound selected from the group consisting of 1-[(3,3-dimethyl-1-cyclohexyl)ethoxycarbonyl]methyl propanoate, 1-[(3,3-dimethyl-1-cyclohexyl) ethoxycarbonyl]methyl butanoate, 1-(3,3-dimethyl-1-cyclohexyl)ethyl 4-oxohexanoate, 1-(3,3-dimethyl-1-cyclohexyl)ethyl 5-oxohexanoate, 1-[(3,3-dimethyl-1-cyclohexyl)ethoxycarbonyl]methyl methyl oxalate, 1-[(3,3-dimethyl-1-cyclohexyl) ethoxycarbonyl]methyl 2-propenoate, and 1-[(3,3-dimethyl-1-cyclohexyl) ethoxycarbonyl]methyl 2-butenoate.

4. 1-[(3,3-Dimethyl-1-cyclohexyl)ethoxycarbonyl] methyl propanoate.

5. A compound according to claim 1, in the form of the stereoisomer of configuration (1S,1'R) or of a mixture containing a preponderant amount of this isomer together with at least one of its other stereoisomers.

6. Perfuming composition or perfumed article containing as a perfuming ingredient a compound according to claim 1.

7. Perfumed article according to claim 6, in the form of a perfume or a cologne, a soap, a bath or shower gel, a shampoo or other hair care product, a cosmetic preparation, a deodorant or antiperspirant, an air freshener, a detergent or fabric softener, or an all-purpose cleaner.

8. A method for the preparation of a perfuming composition or of a perfumed product, wherein there is added to said composition or product a compound according to claim 1.

9. A compound of formula (*III*)

(*III*)

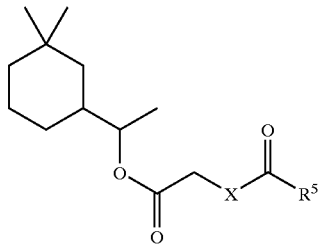

wherein X is an oxygen atom and $R^5$ is a group as defined in claim 1 and having from 1 to 3 carbon atoms.

10. The method of claim 8, wherein the compound is added in an amount sufficient to impart an odor of the musky type accompanied by a slight fruity-ambrette connotation.

* * * * *

UNITED STATES PATENT AND TRADEMARK OFFICE

CERTIFICATE OF CORRECTION

PATENT NO. : RE 38,659 E
DATED : November 23, 2004
INVENTOR(S) : Williams

It is certified that error appears in the above-identified patent and that said Letters Patent is hereby corrected as shown below:

Title page,
Item [57], ABSTRACT, delete Formula I, and substitute therefor:

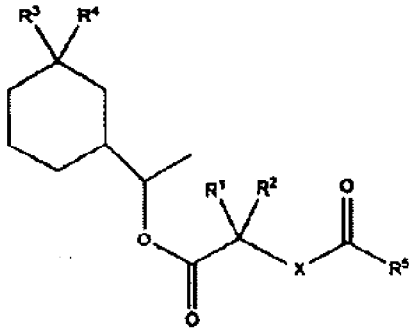

(I)

Column 2,
Lines 4-13, delete Formula I, and substitute therefor:

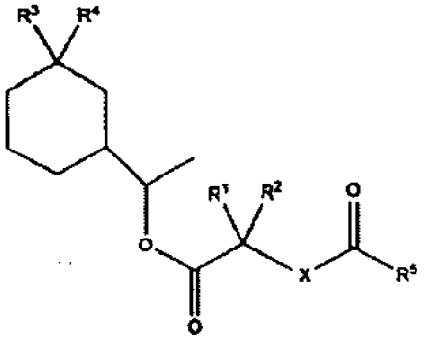

(I)

UNITED STATES PATENT AND TRADEMARK OFFICE

CERTIFICATE OF CORRECTION

PATENT NO. : RE 38,659 E
DATED : November 23, 2004
INVENTOR(S) : Williams

It is certified that error appears in the above-identified patent and that said Letters Patent is hereby corrected as shown below:

Column 5,
Lines 2-13, delete Formula VI and substitute therefor:

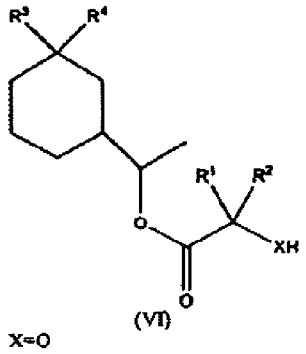

Column 11,
Lines 5-14, delete Formula I, and substitute therefor:

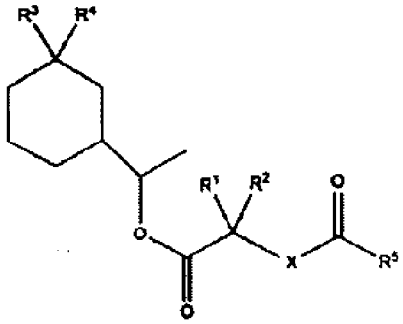

Signed and Sealed this

First Day of March, 2005

JON W. DUDAS
*Director of the United States Patent and Trademark Office*